(12) United States Patent
Barthold et al.

(10) Patent No.: US 10,321,985 B2
(45) Date of Patent: Jun. 18, 2019

(54) VASCULAR PROSTHESIS SYSTEM

(71) Applicant: JOTEC GmbH, Hechingen (DE)

(72) Inventors: Franz-Peter Barthold, Balingen (DE);
Karsten Klein, Moessingen (DE);
Petra Odermatt, Hechingen (DE);
Severin Kleinhans, Balingen (DE)

(73) Assignee: JOTEC GMBH, Hechingen (DE)

( * ) Notice: Subject to any disclaimer, the term of this patent is extended or adjusted under 35 U.S.C. 154(b) by 230 days.

(21) Appl. No.: 15/482,642

(22) Filed: Apr. 7, 2017

(65) Prior Publication Data
US 2017/0209254 A1 Jul. 27, 2017

Related U.S. Application Data

(63) Continuation of application No. PCT/EP2015/073246, filed on Oct. 8, 2015.

(30) Foreign Application Priority Data

Oct. 10, 2014 (DE) .......................... 10 2014 114 747

(51) Int. Cl.
*A61F 2/07* (2013.01)
*A61F 2/852* (2013.01)
(Continued)

(52) U.S. Cl.
CPC ................ *A61F 2/07* (2013.01); *A61F 2/852* (2013.01); *A61F 2002/061* (2013.01);
(Continued)

(58) Field of Classification Search
CPC .................. A61F 2/07; A61F 2002/075; A61F 2002/067; A61F 2002/821; A61F 2002/826; A61F 2002/828; A61F 2/852
See application file for complete search history.

(56) References Cited

U.S. PATENT DOCUMENTS

2006/0142835 A1 6/2006 Spiridigliozzi et al.
2006/0195177 A1* 8/2006 Kaufmann ................ A61F 2/07
623/1.16
(Continued)

FOREIGN PATENT DOCUMENTS

DE 201 15 706 12/2001
DE 103 37 739 3/2005
(Continued)

OTHER PUBLICATIONS

International Preliminary Report for PCT/EP2015/073246, dated Apr. 11, 2017, 16 pages (Including English translation).
International Search Report and Written Opinion for PCT/EP2015/073246, dated Feb. 12, 2015, 22 pages (Including English translation).

*Primary Examiner* — Suba Ganesan
(74) *Attorney, Agent, or Firm* — Rimon, P.C.

(57) ABSTRACT

The invention relates to a vascular prosthesis system for inserting into and for supporting a blood vessel of a patient. The vascular prosthesis system comprises (i) a stent graft element comprising a prosthesis material, and (ii) a stent element free of prosthesis material. Furthermore, a strip-like prosthesis material segment is provided, by means of which the stent graft element and the stent element are connected to each other, in such a way that the strip-like prosthesis material segment forms a prosthesis material bridge.

13 Claims, 4 Drawing Sheets

(51) Int. Cl.
    *A61F 2/06* (2013.01)
    *A61F 2/82* (2013.01)

(52) U.S. Cl.
    CPC ... *A61F 2002/065* (2013.01); *A61F 2002/067* (2013.01); *A61F 2002/075* (2013.01); *A61F 2002/077* (2013.01); *A61F 2002/821* (2013.01); *A61F 2002/828* (2013.01); *A61F 2220/0091* (2013.01); *A61F 2250/006* (2013.01)

(56) References Cited

U.S. PATENT DOCUMENTS

| | | | | |
|---|---|---|---|---|
| 2007/0233229 | A1* | 10/2007 | Berra | A61F 2/07 623/1.13 |
| 2010/0049307 | A1 | 2/2010 | Ren | |
| 2014/0336749 | A1* | 11/2014 | Bogenschuetz | A61F 2/07 623/1.16 |

FOREIGN PATENT DOCUMENTS

| | | |
|---|---|---|
| DE | 10 2012 100839 | 8/2013 |
| DE | 10 2012 103985 | 11/2013 |
| EP | 1295571 A1 | 3/2003 |
| WO | WO 2007/028086 A2 | 3/2007 |
| WO | WO 2010/027651 A1 | 3/2010 |
| WO | WO 2010/150208 A2 | 12/2010 |
| WO | WO 2013/026585 A1 | 2/2013 |
| WO | WO 2013/167493 A1 | 11/2013 |

* cited by examiner

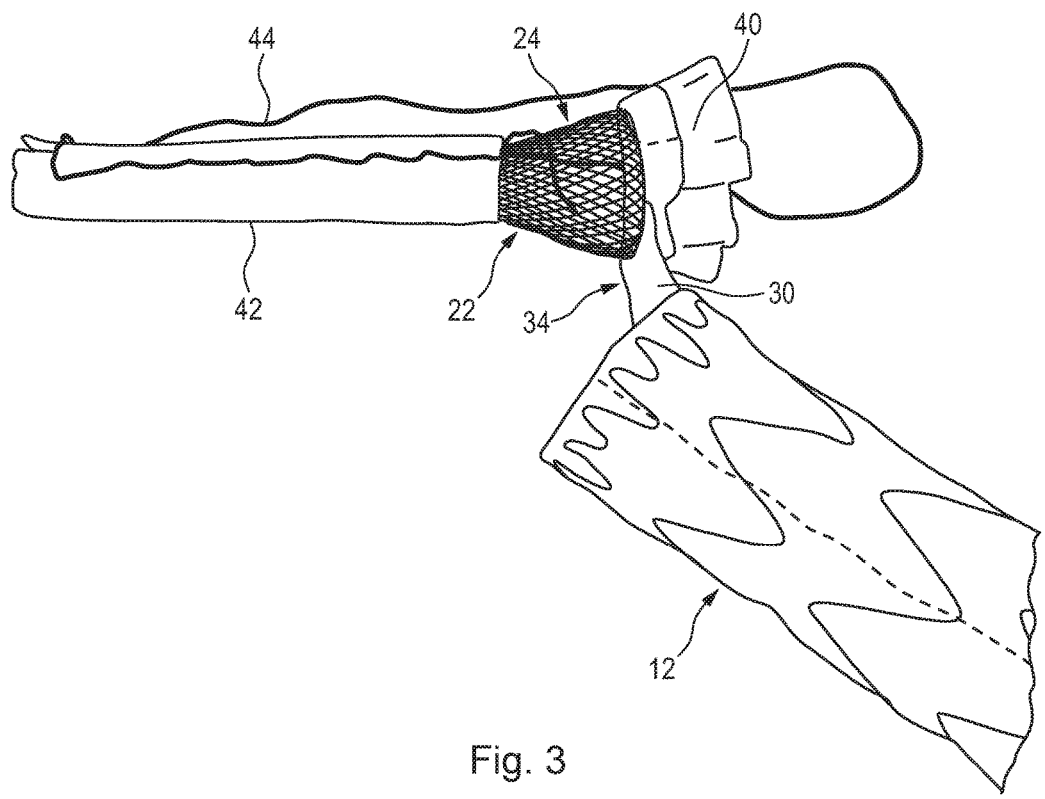
Fig. 3
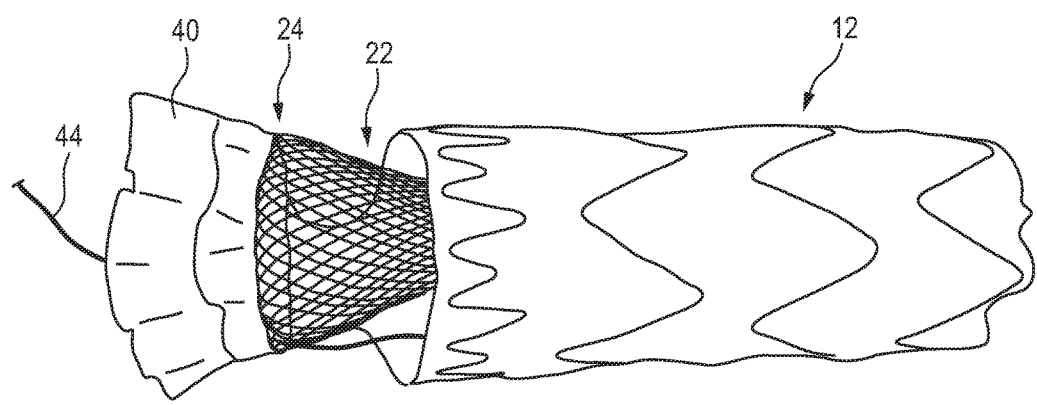

VASCULAR PROSTHESIS SYSTEM

CROSS REFERENCES TO RELATED APPLICATIONS

This application is a continuation of international patent application PCT/EP2015/073246, filed on Oct. 8, 2015 designating the U.S., which international patent application has been published in German language and claims priority from German patent application DE 10 2014 114 747.2, filed on Oct. 10, 2014. The entire contents of these priority applications are incorporated herein by reference.

BACKGROUND OF THE INVENTION

The present invention relates to a vascular prosthesis system for inserting into and supporting a blood vessel of a patient, which vascular prosthesis system is convertible from a compressed state to an expanded state.

In particular, the present relates to a vascular prosthesis system that is implanted in the area of the aortic arch.

Vascular implants of this kind are known in the prior art, for example from DE 103 37 739.5.

It is generally known for intraluminal vascular prostheses, also referred to as endovascular stents or stent grafts, to be implanted in order to treat weakened, damaged or torn vessels or aneurysms. For this purpose, a vascular prosthesis or a stent graft is released at the diseased or damaged site of the vessel and restores the functionality of the original vessel or supports the still existing integrity of the vessel.

An aneurysm is understood here as a widening or bulging of an arterial blood vessel as a consequence of congenital or acquired lesions of the wall. The bulge in this case can affect the vessel wall as a whole or, in what is called a false aneurysm or dissection, blood flows from the lumen of the vessel in between the layers of the vessel wall and tears these apart from one another. Non-treatment of an aneurysm may lead to a rupture of the artery in advanced stages, after which the patient suffers internal bleeding.

The self-expanding vascular implants used for the treatment of such aneurysms generally consist of a hollow cylindrical metal framework of which the jacket surface is covered by a textile or polymer film, such that a hollow cylindrical body is obtained. For implantation, the vascular prosthesis is radially compressed, such that its cross-sectional area is greatly reduced. With the aid of an insertion system, the vascular prosthesis is then brought into the area of the aneurysm, where it is released. By virtue of the resilience of the metal framework, the vascular prosthesis expands again to its original shape and in so doing stretches its jacket surface, which lodges inside the blood vessel proximally arid distally in relation to the aneurysm. In this way, the blood now flows through the vascular prosthesis, and further loading of the bulge is avoided.

The metal framework of such vascular prostheses is generally composed of a wire mesh, for example, or of so-called stent springs, which are arranged in succession and extend circumferentially in a meandering formation and, if appropriate, are connected to each other by connecting struts made of wire, or which are merely connected to each other via the prosthesis material. The wire mesh or the stent springs are usually made of a shape-memory material, generally of Nitinol, as a result of which the stent springs, after introduction into a vessel for release, return to the expanded state and thus "wedge" the vascular implant.

Aneurysms generally occur in the area of the abdominal aorta or thoracic aorta. To treat aneurysms in the abdominal aorta or thoracic aorta, it is already known to stabilize the artery by implantation of a stent such that a rupture of the vessel is avoided.

However, aneurysms can also occur in what is called the ascending branch of the aorta (aorta ascendens). The ascending branch of the aorta is connected directly to the heart. Starting from the aortic root (sinus aortae), the ascending branch extends upward in a slightly curved shape away from the heart and merges there into the aortic arch (arcus aortae). The vessels of the head, among others the left and right carotid arteries, branch off in the area of the aortic arch. The aortic arch follows a curve of approximately 180° with a very narrow radius and connects the ascending branch of the aorta to the thoracic aorta and eventually to the abdominal aorta.

It is important, not only in the area of the aortic arch, to ensure that branch vessels issuing from the main vessel are not blocked by the positioning of the vascular prosthesis, which is why many vascular prostheses have open zones or so-called fenestrations through which branches issuing from the vascular implant, and protruding into the branch vessels, can be inserted and can be fixed on the vascular implant.

An aneurysm or a dissection in the ascending branch of the aorta has hitherto been generally treated by invasive open surgery. Such surgery has previously generally required two major interventions to be performed at different times and entails a very extensive, complex and therefore dangerous operation, since it is not just the heart but also the brain and the abdominal organs of the patient that have to be subjected to hypothermic perfusion, i.e. artificial, cold extracorporeal blood flow, or hypothermic arrest of blood flow. However, only a small number of heart surgeons at specialist centers are sufficiently familiar with such a procedure.

There is therefore still a great need for stent systems/stent graft systems or vascular prostheses with which the surgery outlined above could be made easier and could be performed in a shorter time.

In the prior art, there is as yet no known stent system or stent graft system with which the surgery outlined above could be made easier and could be performed in a shorter time, for which reason these is still a great need for such a system.

SUMMARY OF THE INVENTION

The object of the present invention is therefore to make available a system with which the area of the ascending aorta, of the aortic arch and of the descending aorta can be treated quickly and in an uncomplicated manner, and which also allows the procedures outlined above to be performed by less experienced heart surgeons.

According to the present invention, this object is achieved by a vascular prosthesis system for inserting into and supporting a blood vessel of a patient, which vascular prosthesis system is convertible from a compressed state to an expanded state, said vascular prosthesis system having i) a stent graft element with a hollow cylindrical body, a first, proximal stent graft element end and a second, distal stent graft element end, the stent graft element having supports extending circumferentially in a meandering formation and a prosthesis material for forming a circumferentially covered stent graft element, which prosthesis material is fastened to and connects the supports, and ii) a stent element with a hollow cylindrical body, a first, proximal stem element end and a second, distal stent element end, the stent element having a stent support framework, which is free of prosthesis material, for forming an uncovered stent element; furthermore, in the vascular prosthesis system according to the invention, the stent graft element and the stent element are two structurally separate elements of the vascular prosthesis system, and the stent element is dimensioned and designed in such a way that it is insertable with its second, distal stent element end at least partially into the first, proximal stent graft element end and is expansible therein; furthermore, the stent element, at its first, proximal end, is firmly connected circumferentially to a stent-free prosthesis portion, which prosthesis portion is made solely of prosthesis material, and the stent graft element and the stent element are connected to each other only by a strip-shaped prosthesis material by this portion, in such a way that the strip-shaped prosthesis material portion is fixed with a first end on the first, proximal stent graft element end and is fixed with its second end on the first, proximal stent element end in order to form a prosthesis material bridge.

The object of the invention is achieved in full in this way.

With the new vascular prosthesis system, it is easily possible to make available a portion which is free of prosthesis material and via which the branching-off vessels can continue to be supplied with blood, while at the same time the damaged vessels are supported by the so-called covered stent graft portion, i.e. the portion that has prosthesis material by this. The insertion and placement of this system can be managed easily and with precision by virtue of its two-part structure. By means of the stent graft element being connected to the stent element "only", i.e. exclusively, via a strip-shaped or strip-like prosthesis material portion, both elements, i.e. the stent graft element and the stent element, are freely movable in relation to each other, particularly in the unloaded state, and can also be compressed separately from each other. The vascular prosthesis system according to the invention therefore affords the advantage that it can be adapted in terms of its longitudinal direction and curvature to the respective anatomical circumstances presented by the patient who is to be treated.

Here, "only" via a strip-shaped prosthesis material portion signifies that the stent graft element and the stent element are not connected to each other by prosthesis material except for the strip-shaped connection. This means that the two elements are produced separately from each other and can also be handled separately from each other, wherein the strip-shaped prosthesis material portion provides for a bridge between the otherwise unconnected elements. This almost free mobility of the stent element with respect to the stent graft element has the effect that the stent element can be expanded independently of the stent graft element and at least partially within the stent graft element. Moreover, this results in the vascular prosthesis system having a flexibility that allows the stent element to be released in a strongly curved state without substantially influencing the stent graft element, wherein the strip-shaped prosthesis material portion however provides a connection between the two elements that allows the stent element to slide or slip out of the stent graft element. Moreover, after release, this bridge forces the stent element to curve, as a result of which it is possible to obtain a stent portion which is free of prosthesis material and which is individually adaptable in length and curvature.

To insert the vascular prosthesis system into a vessel of a patient who is to be treated, said system is compressed, the stent element and the stent graft element being compressed in each case by dedicated sheaths which can be pulled back independently of each other in order, on the one hand, to firstly release the stent graft element and, on the other hand, to release the stent element in a second step, which can be carried out independently of the first one. Accordingly, both elements are loaded concentrically on an insertion catheter, wherein the stent element, compressed by its dedicated stent element sheath, comes to lie inside the stent graft element, which is likewise compressed by a further sheath.

To release the vascular prosthesis system, the insertion catheter, with the system loaded thereon, is first of all inserted into the vessel to be treated, for example with monitoring via corresponding markers on the vascular prosthesis system, and is correctly placed, and expanded by retraction of the stent graft element sheath, in such a way that it does not block vessels branching off from the main vessel. Then, in a second step, the stent element is at least partially released inside the stent graft element, by retraction of the sheath compressing the stent element, wherein the stent element is located with at least one portion outside the stent graft element, and this portion then comes to lie in the area of the branching-off vessels. This is also achieved by the fact that the stent element is able to bend, wherein the strip-shaped prosthesis material portion comes to lie not in the area of the branching-off vessels, but instead on the opposite vessel wall.

It is therefore not necessary to insert two separate stent graft elements or stent elements separately from each other, using two different insertion catheters, and instead the system according to the invention can be inserted using one insertion system or insertion catheter. However, the strip-shaped prosthesis material forming the bridge between stent graft element and stent element at the same time ensures that the stent element does not slip completely out of the stent graft element. Since the stent element expands partially within the stent graft element, the former is anchored in the interior of the stent graft element but, at least with the portion not released in the stent graft element, remains flexible in respect of bending and adaptation to the aortic arch, for example. With the stent-free prosthesis portion which is also provided on the stent element, and which is preferably provided like a collar on the other end of the stent element, the vascular prosthesis system can be sutured to the vessel wall and the vascular prosthesis as a whole can thereby be connected to the vessel wall by a single suture. This represents a considerable advantage since the duration of this suturing directly influences the duration of the surgical intervention and, for example, also the duration of the head perfusion.

By means of the stent graft system according to the invention, i.e. the combination of two individual elements structurally separate from each other but connected by the bridge, it is thereby also possible, for example in the case of implantation in the aortic arch, to treat the three portions of the aorta simultaneously, namely the ascending aorta, the aortic arch and the descending aorta. It is thus possible to dispense with resection of the aortic arch, with all the associated complex perfusion requirements for the brain and lower body, and the intervention can be carried out simply by separating the uppermost portion of the ascending aorta in a short (ca, 10-20 minute) selective head perfusion phase or hypothermic arrest phase in order to insert and release the new vascular prosthesis. It can be inserted arid released simply with monitoring by the naked eye or by angioscope.

Compared to vascular prosthesis systems for the aortic arch that are already known in the prior art, the vascular prosthesis system according to the invention also overcomes the disadvantage whereby, during release, there is a certain flexibility in terms of the landing zones, which flexibility has to be critically assessed particularly in the case of one-part vascular prostheses.

According to the invention, therefore, an intraluminal vascular prosthesis is made available with which it is possible to simplify surgical interventions, in particular on the aortic arch, or in the ascending aorta, aortic arch and descending aorta, and to greatly reduce the time needed for these interventions. Advantageously, therefore, it is not just highly specialized heart surgeons who can perform the above-described interventions on the aortic arch. Moreover, the vascular prosthesis according to the invention can also be used on severely diseased patients, and also on elderly patients presenting with age-related damage to the layers of the aortic wall, for example and with non-perfusion of vital organ systems such as the brain or abdominal organs, since these can be used with a shortened and surgically simpler method.

Advantageously, the stent element free of prosthesis material is released in the process in the expanded state in the area of the aortic arch. This ensures that the blood flow into the branching-off vessels, such as the brachiocephalic trunk, the left common carotid artery and the left subclavian artery, is not impeded. The blood flowing through the aortic arch, and through the vascular prosthesis system to be anchored therein, can leave the latter through the openings present in the uncovered stent element of the vascular prosthesis.

The strip-shaped prosthesis material portion, which is stent-free by definition, therefore preferably extends from the first, proximal stent graft element end to the first, proximal stent element end.

It will be appreciated that, in order to form the prosthesis material bridge, the strip-shaped prosthesis material portion is fixed only at its two ends to the vascular prosthesis, as has been defined above, such that its portion lying between the two ends lies free, or unfixed on the vascular prosthesis, i.e. on the stent element.

Although they will be clear to a person skilled in the art per se and from the present disclosure, some of the terms used here are defined in more detail below.

As discussed at the outset, a "stent spring" is understood here as being any one-piece annular element that can be compressed on the basis of its material and, after removal of the compressive pressure, can expand again in the manner of a spring. "In a meandering formation" is understood here as meaning any serpentine or loop-shaped profile of the stent spring or of the stent wire, each stent spring being formed in one piece, i.e. from a stent spring ring extending circumferentially in a meandering formation.

In this context, a "one-piece stent spring extending circumferentially in a meandering formation" is here understood as an annular stent element that is expansible and compressible in a spring-like manner and has a wave-like profile, with the wave crest and wave trough, which form a phase, alternating.

Advantageously, in this case a pointed arch is respectively formed by two legs and a vertex or lowest point lying between the legs.

Here, "at least one pointed arch" means that the side body is extended by the setting out of a single pointed arch of a stent spring, or else by two or more pointed arches. In a preferred embodiment, two pointed arches of a stent spring are set out. In principle, the plurality of the pointed arches extending circumferentially in a meandering formation form the stent spring of the main body, and the set-out pointed arch/pointed arches form(s) the branching point for the side body.

In the case of stent grafts or endoluminal prostheses, the respective ends are in principle generally designated, as here, by the terms "distal" and "proximal", where the term "distal" designates that part or end lying farther downstream in relation to the blood flow. By contrast, the term "proximal" designates, again in relation to the blood flow, a part or the end lying farther upstream in relation to the blood flow. To put it another way, the term "distal" means in the direction of the blood flow, and the term "proximal" means counter to the direction of the blood flow. In catheters, by contrast, or insertion systems, the term "distal" designates the end of the catheter or insertion system that is introduced into the patient, or the end farthest away from the user, and the term "proximal" designates the end directed closer toward, the user.

Correspondingly, in the present case, the "proximal" opening and the "distal" opening of the vascular implant are the openings by which the flow of blood through the hollow-cylindrical body of the vascular implant is ensured: when the vascular implant according to the invention is implanted in a blood vessel, for example the aorta, the blood coming from the heart therefore flows through the proximal opening of the vascular implant and leaves the vascular implant through the distal openings thereof.

The vascular prosthesis system or the two hollow-cylindrical elements thereof can in this case have a uniform diameter, or else different diameters, along the entire length thereof.

By definition, the stent springs are not directly connected to one another, and they do not have any connecting legs or struts or similar connecting elements between one another. The stent springs are connected to one another only by way of the prosthesis material to which the stent springs are attached, whereby an "indirect connection" is created between the stent springs.

In the present case, a "stent" or "stent support framework" denotes any device or structure that provides a force of expansion and/or a supporting function for a prosthesis. Accordingly, a stent element is therefore any element that has the properties of a stent.

The expression "stent graft" is intended in the present case—as also in the prior art—to mean a prosthesis that has one or more stents (or stent springs) and also a prosthesis ("graft") material connected thereto, which forms a lumen through at least one portion of the prosthesis. Such a stent graft is also designated as a covered stent (portion).

Moreover, "strip-shaped", strip-like or "strip-shaped prosthesis material portion" is understood as being any element of prosthesis material that is longer than it is broad and that forms a bridge-like or flap-like connection between the stent graft element and the stent element. The strip-shaped prosthesis material portion here is a kind of continuation of the prosthesis material of the stent graft portion, wherein the strip-shaped prosthesis material by definition is not formed about the entire circumference of the hollow cylindrical body of the stent graft portion but only about a relatively small part of the circumference, in order specifically to form a strip-shaped portion.

According to one embodiment of the vascular prosthesis system according to the invention, the stent-free prosthesis portion is formed in the shape of a collar on the first, proximal stent element end.

According to a further embodiment, the vascular prosthesis system according to the invention is designed, as has been mentioned above, for implantation in an aorta, particularly in the area of the ascending aorta, the aortic arch and the descending aorta. For insertion into the aorta, the vascular prosthesis system in this case is convertible from a compressed state to an expanded state, and the stent graft element and the stent element are designed for anchoring the vascular prosthesis system in the aorta.

In this context, provision is preferably made, in further embodiments, that the stent element free of prosthesis material is releasable in the expanded state in the area of the aortic arch.

In the vascular prosthesis system according to the invention, provision is made in this context that the covered stent graft element comes to lie distally in relation to the subclavian artery and that the uncovered stent element comes to lie in the aortic arch. The stent-free prosthesis portion is positioned and fixed in the proximal aortic arch.

In other words, the stent graft element is therefore located in the released state at the distal end area of the vascular prosthesis system and can therefore also be designated as a distal vascular prosthesis portion in the released form of the two elements.

In the released state, in which the stent element and the stent graft element are anchored in each other with each other or by partial overlapping, the covered stent graft element and the stent-free prosthesis material portion thus form the outer ends of the vascular prosthesis system according to the invention.

According to a further embodiment, at least the supports of the stent graft element and/or the stent support framework of the stent element have are made from a self-expanding material or such a material. It is particularly preferable here if the material is Nitinol.

In a further embodiment, as has already been discussed above, the stent element free of prosthesis material is releasable in the expanded state in the area of the aortic arch.

In the vascular prosthesis system according to the invention, it is also preferable in one embodiment if the stent graft element has between two and eight successive supports.

In particular, it is preferable if two, three, four, five, six, seven or eight supports are provided which extend circumferentially in a meandering formation one after another. According to a preferred embodiment, the supports or stent springs are not themselves interconnected by webs or the like, or are not in direct contact with one another, and instead are connected only by the prosthesis material to form a hollow cylindrical body. This embodiment has the advantage that a person skilled in the art can adapt the length of the stent graft portion to the particular circumstances of the vessel.

According to a further embodiment of the vascular prosthesis system according to the invention, it is preferable if the stent element free of prosthesis material has a braided, twisted or laser-cut stent support framework.

A "stent support framework" is understood here as any design of a stent in which different wire strands are intertwined, interlaced or otherwise coupled to form a structure with zones, areas or points at which the strands lie over one another, and with zones or areas that are free of the wire strands and that therefore form openings or windows or meshes. Accordingly, a laser-cut stent support framework also has meshes or openings through which the blood carried in the aorta or in the aortic arch can leave the aorta and pass into the branching-off vessels, in particular the brachiocephalic trunk, the left common carotid artery and the left subclavian artery, and thus ensures supply of blood to these vessels.

Moreover, in a further embodiment of the vascular prosthesis system according to the invention, it is preferable if the strip-shaped prosthesis material portion connects the stent graft element and the stent element only over an arc of a circle of less than or equal to 180°.

As has already been discussed above, the bridge, which is provided by the strip-shaped prosthesis material, is not formed about the entire circumference. This has the advantage that the bridge does not cover wide parts of the uncovered stent element and instead leaves these free in order to permit an unobstructed flow of blood through the openings in the stent element, while at the same time ensuring a connection between stent graft element and stent element. Moreover, after release, this bridge forces the stent element into a curved shape, as a result of which it is possible to obtain a stent portion which is free of prosthesis material and which is individually adaptable in length and curvature.

According to a preferred embodiment of the vascular prosthesis system according to the invention, it is therefore preferable if the strip-shaped prosthesis material portion is a strip-shaped continuation of the prosthesis material of the stent graft element.

As has likewise been discussed above, it is preferable, according to another and more refined embodiment of the above-discussed vascular prosthesis system according to the invention, if the stent graft element and the stent element are releasable separately from each other, in such a way that the stent element is releasable after the stent graft element and at least partially within the latter.

Here, "releasable . . . at least partially within the latter" means that the stent element in the expanded state is positioned partially or to a greater extent within the stent graft element, in which case a part of the stent element is expanded outside the stent graft element and therefore represents the portion of the vascular prosthesis system through which blood is able to leave through the uncovered openings of the stent element, for example into branching-off vessels.

In the vascular prosthesis system according to the invention, it is generally preferable if the prosthesis material has a material chosen from a textile or a polymer.

In particular, it is preferable if the prosthesis material has a material, or is formed from a material, chosen from polyester, polyurethane, polystyrene, polytetrafluoroethylene, ultra-high-molecular-weight polyethylene (UHMPE), or mixtures thereof.

The prosthesis material of the stent graft element, the strip-shaped prosthesis material portion and the stent-free prosthesis portion can all be formed of such a material or have such a material.

According to a particularly preferred embodiment, the stent graft element has a length of between ca. 20 mm and ca. 100 mm, and the uncovered stent element has a length of between ca. 30 mm and ca. 100 mm.

The invention further relates to the use of a vascular prosthesis system according to the invention for the treatment of dissections or aneurysms of the thoracic aorta.

Moreover, the present invention also relates to a method for releasing the vascular prosthesis system according to the invention, said method having the following steps:

introducing the vascular prosthesis system in the compressed state into an aorta of a patient, in such a way that the entire stent graft element is positioned distally in relation to the subclavian artery;

converting the stent graft element to the expanded state by retracting a first sheath that compresses the stent graft element;

converting the stent element to the expanded state, by retracting a second sheath that compresses the stent element;

in such a way that the stent element free of prosthesis material is released in the aortic arch in the area of the origins of the brachiocephalic trunk, the common carotid artery and the left subclavian artery, and wherein the stent-free prosthesis portion is positioned in the proximal direction in relation to the origin of the brachiocephalic trunk.

This method ensures that the vascular prosthesis system according to the invention is positioned in such a way that the uncovered stent element allows blood to flow into the branching-off vessels of the brachiocephalic trunk, the common carotid artery and the left subclavian artery.

It will be noted here that the covered stent graft element ends slightly in the distal direction from the origin of the subclavian artery. The uncovered stent element is now released in the aortic arch, the wire meshes or the openings of the laser-cut stent element being so wide that there is no danger of blocking the origins of the vessels of the head and neck (brachiocephalic trunk, left common carotid artery, left subclavian artery). Thereafter, collar-shaped prosthesis portion is sutured onto the proximal aortic arch.

Thus, the vascular prosthesis system according to the invention and the method for introducing and releasing it afford the advantage that a tear or an aneurysm present in the area of the ascending aorta can be treated, as before, by resection and conventional prosthetic management, and, at the same time, any remaining tears of the intima in the proximal descending aorta or in the aortic arch can be safely stabilized, specifically without danger of rupture in the long term. Particularly in the case of a dissection or complex aneurysm of the thoracic aorta, the surgical outlay and time involved can be therefore greatly reduced compared to operations and systems used hitherto in the prior art, with comparable results, and therefore the risk of the intervention can be significantly lessened.

Further advantages will become clear from the figures and from the following description of preferred illustrative embodiments.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Illustrative embodiments of the invention are shown in the drawing and are explained in more detail in the description below, in which:

FIG. 3 shows a schematic view of the embodiment shown in FIGS. 1 and 2, in which the stent element is partially compressed by a stent element sheath;

FIG. 4 shows a schematic view of the embodiment shown in FIGS. 1 to 3, the compressed stent element here being positioned partially inside the stent graft element for loading onto a catheter, and the end of the stent element that carries the stent-free prosthesis portion being already partially released.

DESCRIPTION OF PREFERRED EMBODIMENTS

Figure 1:
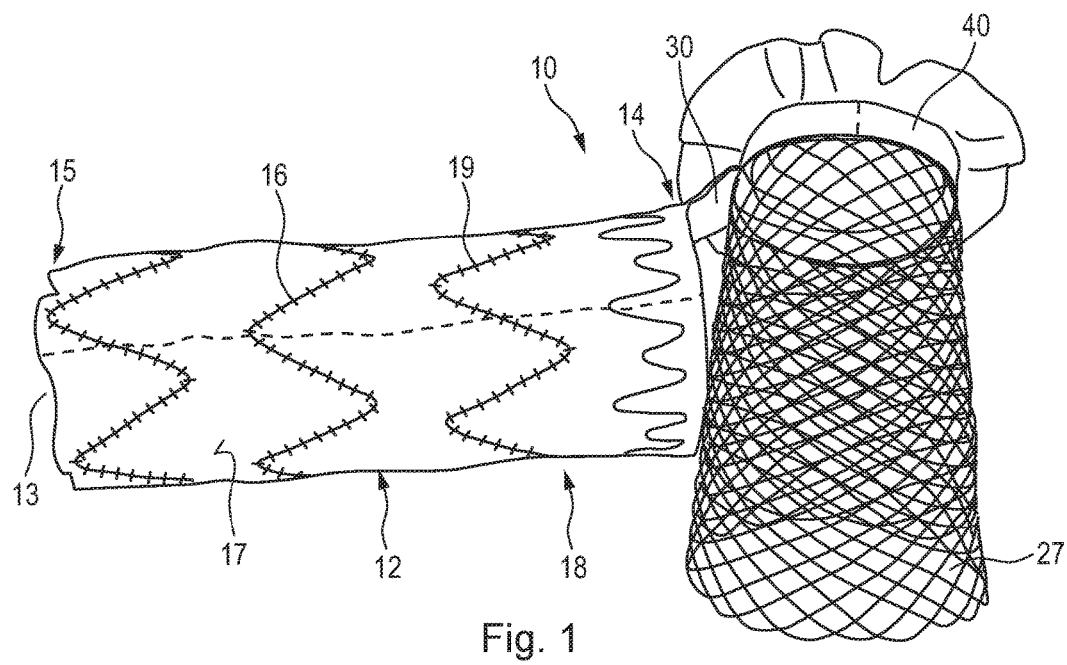
FIG. 1 shows a schematic view of an embodiment of a vascular prosthesis according to the invention, in the non-inserted, expanded state.
Figure 2:
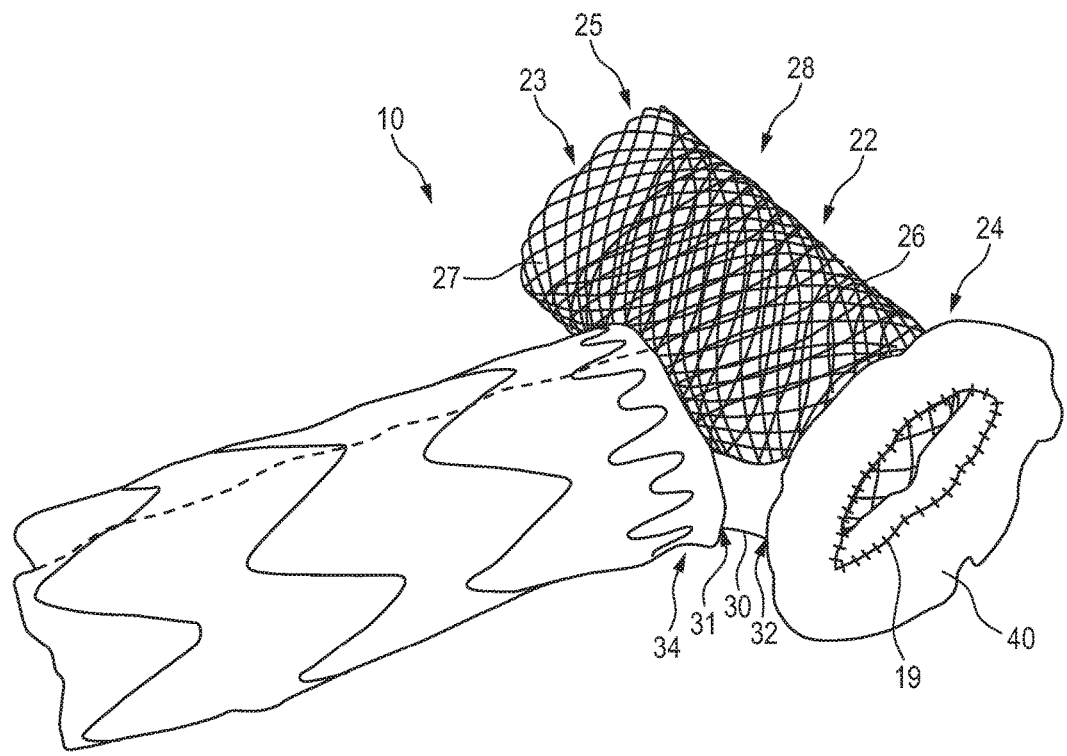
FIG. 2 shows a schematic view of another perspective of the embodiment shown in FIG. 1, likewise in the non-inserted but expanded state.

In the figures, identical features are provided with identical reference signs. For the sake of clarity, the figures do not always show all of the reference signs. In FIGS. 1 and 2, reference sign 10 designates the whole of a vascular prosthesis system, having a stent graft element 12 with a hollow cylindrical body 13, a first, proximal stent graft element end 14 and a second, distal stent graft element end 15. Moreover, the stent graft element 12 has supports 16 extending circumferentially in a meandering formation, and a prosthesis material 17 fastened to and connecting the supports 16, as a result of which a circumferentially covered stent graft element 18 is formed. The prosthesis material 17 is preferably sutured onto the supports 16, as is indicated by sutures 19. The sutures 19 are indicated only in FIG. 1.

The vascular prosthesis system 10 moreover has a stent element 22 with a hollow cylindrical body 23, a first, proximal stent element end 24 and a second, distal stent element end 25. The stent element 22 has a stent support framework 26, which is free of prosthesis material, as a result of which an uncovered stent element 28 is formed, with openings or meshes or holes 27.

It will also be seen from FIGS. 1 and 2 that the stent graft element 12 and stent element 22 are two separate structural units. Only a strip-shaped prosthesis material portion 30 connects the two elements 12 and 22, wherein the prosthesis material portion 30 has two ends, namely a first end 31 and a second end 32, and wherein the portion 30 is fixed with its first end 31 only on the first, proximal stent graft element end 14 and with its second end 32 on the first, proximal stent element end 24. A prosthesis material bridge 34 is thus formed which extends from the first, proximal stent graft element end 14 to the first, proximal stent element end 24.

It will also be seen from FIGS. 1 and 2 that the stent element 22, at its first, proximal end 24, has a stent-free prosthesis portion 40 which extends circumferentially thereon and which is connected to the proximal stent element end 24, preferably sutured onto the latter. This stent-free prosthesis portion 40 forms a kind of collar which, in the inserted state, can be sutured onto the vessel wall.

The strip-shaped prosthesis material portion 30 is also sutured onto the proximal stent graft element end 14, on the one hand, and onto the proximal stent element end 24, on the other hand, via corresponding sutures 19.

In the state shown in FIGS. 1 and 2, the two elements 12 and 22 are practically freely movable in relation to each other, and they are connected to each other flexibly, i.e. movably, only via the bridge 34.

FIG. 3, finally, shows that the stent element 22 is compressed along almost its entire length by a stent element sheath 42 being pulled over it, and only the proximal stent element end 24, on which the stent-free prosthesis portion 40 and an end of the strip-shaped prosthesis material portion 30 is arranged, is not yet compressed. The figure likewise shows a thread 44, via which the sheath 42 can be pulled back off from the stent element 22 by tensile force, as a result of which said stent element 22 is released. The stent element sheath 42 can preferably be made here of a textile material.

For loading onto an insertion catheter (not shown), the two elements 12 and 22 are loaded onto the latter concentrically. The stent element 22 lies compressed inside the stent graft element 12, which stent graft element 12 is in turn kept compressed by a stent graft element sheath (not shown).

In order to release the vascular prosthesis system, the stent graft element sheath is first of all pulled back, as a result of which it can expand in the vessel and bear on the vessel walls or can press against the latter by means of radial force. In a next step, the stent element sheath 42 is then removed by pulling the thread 44, as a result of which the stent element 22 is released and, for example, forced into a curvature in the aortic arch. By way of the collar-like stent-free prosthesis portion 40, the vascular prosthesis 10 is then fixed to the vessel wall with a suture.

FIG. 4 shows the partial release of the stent element 22: The proximal end 24 of the stent element 22 is completely released, whereas quite a large portion is still in the compressed state inside the stent graft element 12.

Figure 5:
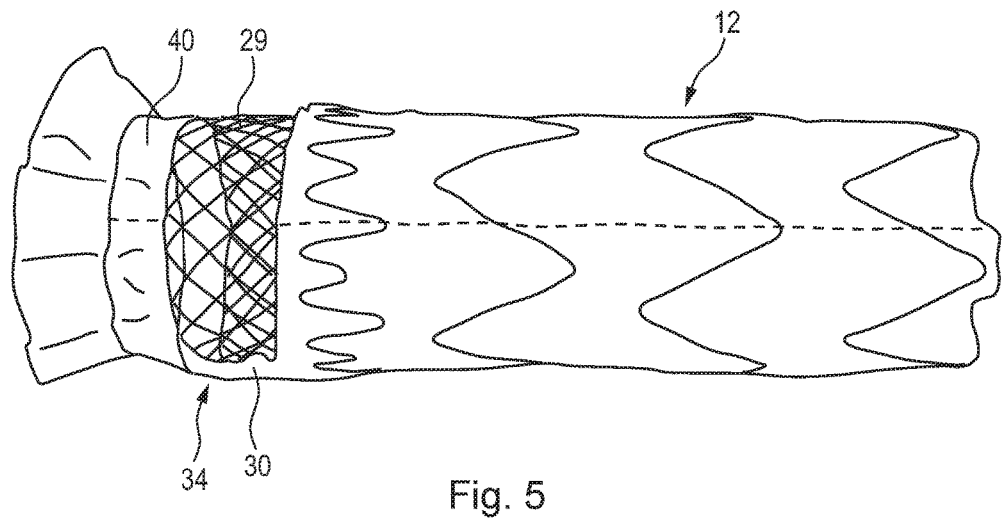
FIG. 5 shows a schematic view of the completely released and expanded vascular prosthesis system in the uncurved form of the stent element.

In FIG. 5, the stent element 22 is finally completely released, and the stent element 22 presses outward on account of its radial force and therefore, at the places where it is located inside the stent graft element 12, it presses against the stent graft element 12 from the inside. At the same time, a part of the stent element 22 is not inside the stent graft element 12, as is indicated by reference sign 29.

If the stent element 22 is now pulled partially out of the stent graft element 12, it is forced into a curvature 48 by the prosthesis material bridge 34. This state is shown in FIG. 6.

Figure 6:
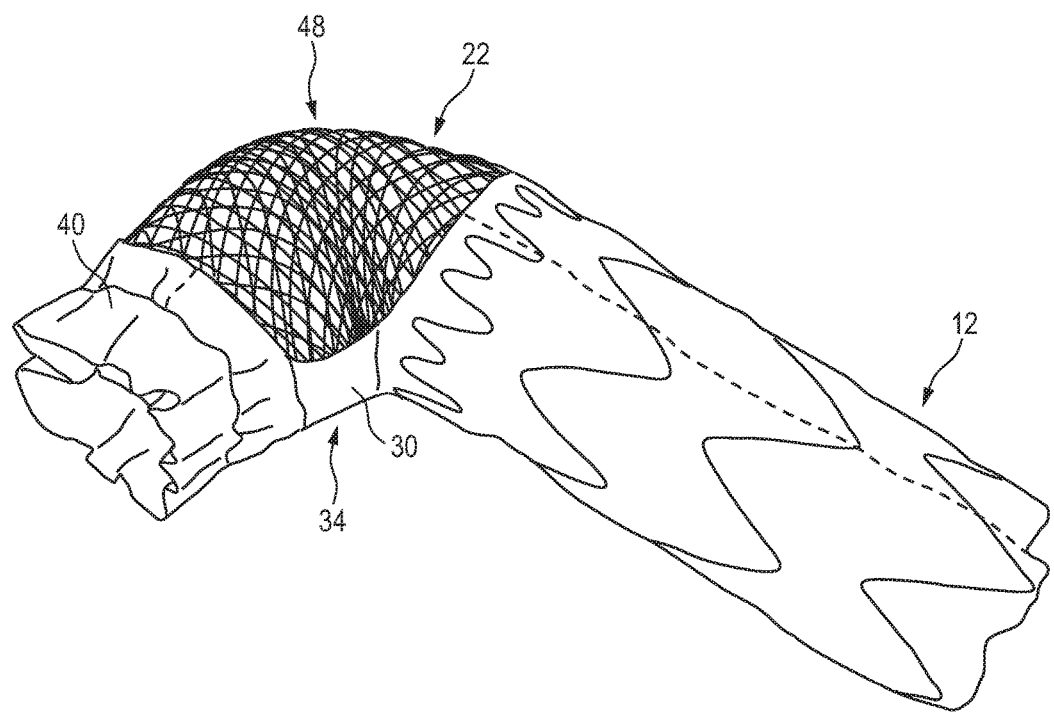
FIG. 6 shows a schematic view of the completely released and expanded vascular prosthesis system with a curved stent element portion, specifically outside a vessel.

It will also be seen from FIG. 6 that, in relation to the curve/bend axis or curve/bend midpoint, the bridge 34 comes to lie radially inwardly, and the open, uncovered holes 27 at least come to lie in the larger, radially outer bend area.

Figure 7:
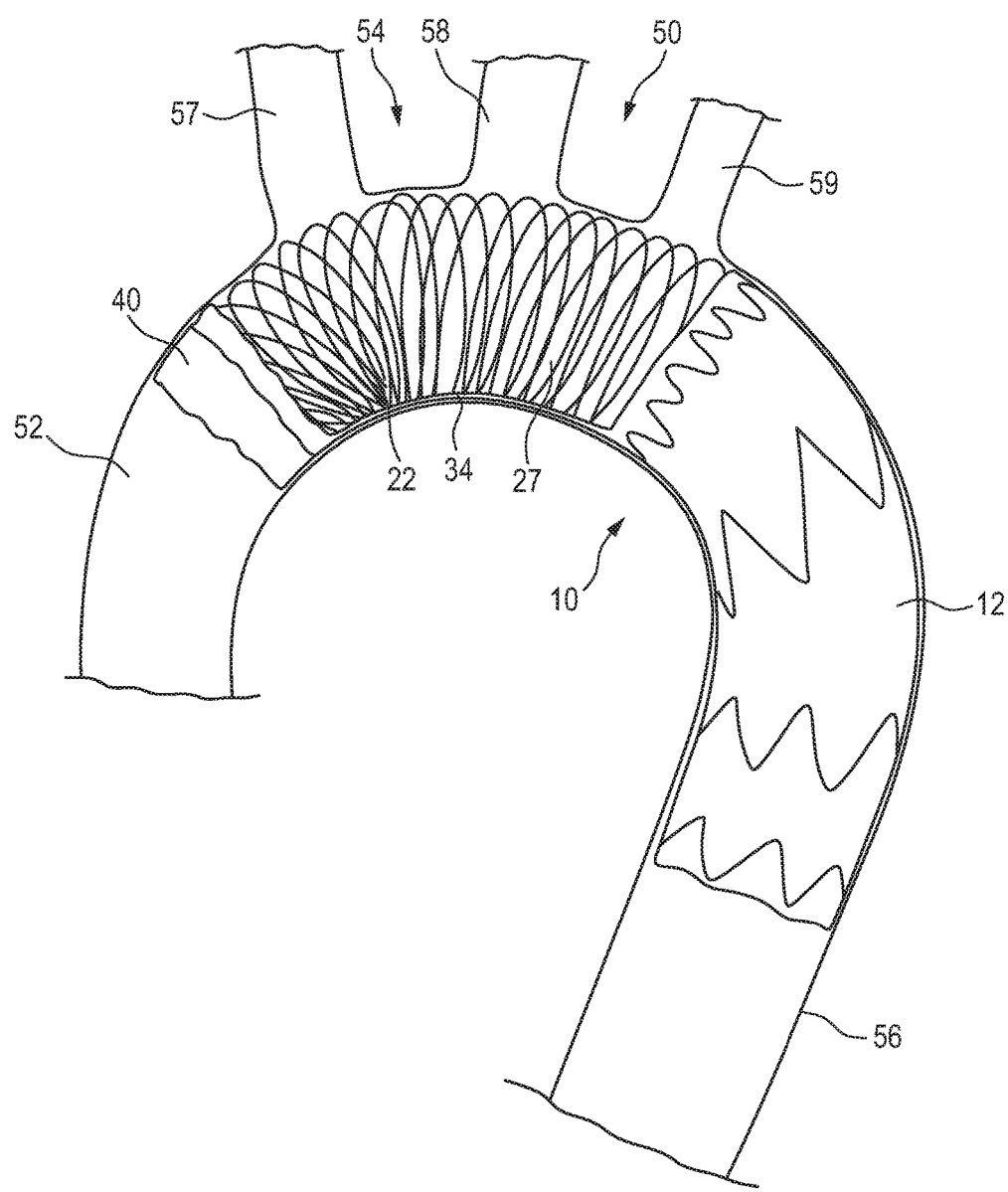
FIG. 7 shows a schematic view of the vascular prosthesis system completely released and expanded in the aorta.

FIG. 7 finally shows the embodiment of the vascular prosthesis system according to the invention shown in FIGS. 1 to 5 in a state when inserted into an aorta 50: In FIG. 7, reference sign 52 designates a part of the ascending aorta, reference sign 54 designates the aortic arch, and reference sign 56 designates the descending aorta. As can be seen from FIG. 7, three vessels 57, 58 and 59 branch off in the area of the aortic arch 54, namely the brachiocephalic trunk 57, the common carotid artery 58, and the left subclavian artery 59.

FIG. 7 also indicates the placement and positioning of the embodiment of the vascular prosthesis system 10 according to the invention shown in FIGS. 1 to 5: It will be noted that the stent graft element 12, or the distal end 15 thereof, begins in the proximal direction in relation to the brachiocephalic trunk, furthermore that the stent element 22 free of prosthesis material is released in the aortic arch 54 and can supply blood to the branching-off vessels 57, 58 and 59 through its cells or openings or meshes 27, and that, finally, the stent-free prosthesis portion 40 begins in the distal direction in relation to the left subclavian artery 59.

For inserting the vascular prosthesis 10 according to the invention, it is loaded, as has been mentioned above, onto an insertion system (not shown), specifically in such a way that the two elements 12 and 22 are maintained concentrically in a compressed state thereon, with separate retraction sheaths to be operated separately. Methods and devices for inserting vascular prostheses are familiar to a person skilled in the art from the prior art.

The vascular prosthesis 10 maintained in a compressed state is advanced into the descending aorta, and the correct placement can be monitored, for example, by suitable markers, e.g. radiopaque markers, provided on the vascular prosthesis 10. After correct placement, the stent graft element 12 is then firstly released by pulling back the stent graft element sheath, and thereafter the stent element 22 by pulling back the stent element sheath 42, which stent element 22 is released as an uncovered vascular prosthesis portion in the aortic arch 54, wherein the openings or meshes 27 are so wide that there is no danger of blocking the origins of the vessels 57, 58 and 59 of the head and neck (brachiocephalic trunk, left common carotid aorta, left subclavian artery).

Lastly, in the proximal direction from the origin of the brachiocephalic trunk 57, the stent-free prosthesis portion is sutured to the proximal aortic arch.

It will be clear to a person skilled in the art that he can determine and specifically implement the exact dimensions and spatial requirements of the individual vascular prosthesis elements 12, 22 and 40 and also the length of the prosthesis material bridge 34 by preliminary examination of the patient who is to be treated.

What is claimed is:

1. A vascular prosthesis system for inserting into and supporting a blood vessel of a patient, which vascular prosthesis system is convertible from a compressed state to an expanded state, said vascular prosthesis system having the following:

a stent graft element with a hollow cylindrical body, a first, proximal stent graft element end and a second, distal stent graft element end, the stent graft element having supports extending circumferentially in a meandering formation, and a prosthesis material for forming a circumferentially covered stent graft element, which prosthesis material is fastened to and connects the supports, and a stent element with a hollow cylindrical body, a first, proximal stent element end and a second, distal stent element end, the stent element having a stent support framework, which is free of prosthesis material, for forming an uncovered stent element, wherein the stent graft element and the stent element are two structurally separate elements of the vascular prosthesis system, and the stent element is dimensioned and designed in such a way that it is insertable with its second, distal stent element end at least partially into the first, proximal stent graft element end and is expansible therein, wherein furthermore the stent element at its first, proximal end, is firmly connected circumferentially to a stent-free prosthesis portion, which prosthesis portion is made solely of prosthesis material, and wherein furthermore the stent graft element and the stent element are connected to each other only by a strip-shaped prosthesis material portion, in such a way that the strip-shaped prosthesis material portion is fixed with a first end on the first, proximal stent graft element end and is fixed with its second end on the first, proximal stent element end in order to form a prosthesis material bridge.

2. The vascular prosthesis system as claimed in claim 1, wherein the stent-free prosthesis portion is formed in the shape of a collar on the first, proximal stent element end.

3. The vascular prosthesis system as claimed in claim 1, wherein it is designed for implantation in an aorta, particularly in the area of the ascending aorta, the aortic arch and the descending aorta.

4. The vascular prosthesis system as claimed in claim 1, wherein at least the supports of the stent graft element and/or the stent support framework of the stent element are made from a self-expanding material or have such a material.

5. The vascular prosthesis system as claimed in claim 1, wherein the stent element free of prosthesis material is releasable in the expanded state in the area of the aortic arch.

6. The vascular prosthesis system as claimed in claim 1, wherein the stent graft element has between two and eight successive supports.

7. The vascular prosthesis system as claimed in claim 1, wherein the stent element free of prosthesis material has a braided, twisted or laser-cut stent support framework.

8. The vascular prosthesis system as claimed in claim 1, wherein the strip-shaped prosthesis material portion connects the stent graft element and the stent element only over an arc of a circle of less than or equal to 180°.

9. The vascular prosthesis system as claimed in claim 1, wherein the strip-shaped prosthesis material portion is a strip-shaped continuation of the prosthesis material of the stent graft element.

10. The vascular prosthesis system as claimed in claim 1, wherein the stent graft element and the stent element are releasable separately from each other, in such a way that the stent element is releasable after the stent graft element and at least partially within the latter.

11. A method for treating dissections or aneurysms of the thoracic aorta of a patient in need thereof, comprising the steps of i) introducing the vascular prosthesis system of claim 1 into an aorta of an patient in need thereof, and of ii) releasing the vascular prosthesis system in the aorta.

12. The method of claim 11, having the following steps:
introducing the vascular prosthesis system in the compressed state into an aorta of a patient, in such a way that the entire stent graft element is positioned distally in relation to the subclavian artery;
converting the stent graft element to the expanded state by retracting a first sheath that compresses the stent graft element;
converting the stent element to the expanded state, by retracting a second sheath that compresses the stent element;
in such a way that the stent element free of prosthesis material is released in the aortic arch in the area of the origins of the brachiocephalic trunk, the common carotid artery and the left subclavian artery, and
wherein the stent-free prosthesis portion is positioned in the proximal direction in relation to the origin of the brachiocephalic trunk,
thereby treating the dissection or aneurysma.

13. A method for releasing the vascular prosthesis system as claimed in claim 1, wherein the method has the following steps:
introducing the vascular prosthesis system in the compressed state into an aorta of a patient, in such a way that the entire stent graft element is positioned distally in relation to the subclavian artery;
converting the stent graft element to the expanded state by retracting a first sheath that compresses the stent graft element;
converting the stent element to the expanded state, by retracting a second sheath that compresses the stent element;
in such a way that the stent element free of prosthesis material is released in the aortic arch in the area of the origins of the brachiocephalic trunk, the common carotid artery and the left subclavian artery, and
wherein the stent-free prosthesis portion is positioned in the proximal direction in relation to the origin of the brachiocephalic trunk.

* * * * *